United States Patent [19]

Konrad et al.

[11] 4,325,704
[45] Apr. 20, 1982

[54] HAIR DYES

[75] Inventors: Günther Konrad, Hilden; Edgar Lieske, Düsseldorf, both of Fed. Rep. of Germany

[73] Assignee: Henkel Kommanditgesellschaft auf Aktien, Düsseldorf, Fed. Rep. of Germany

[21] Appl. No.: 179,436

[22] Filed: Aug. 19, 1980

[30] Foreign Application Priority Data

Aug. 24, 1979 [DE] Fed. Rep. of Germany ....... 2934330

[51] Int. Cl.³ ............................................... A61K 7/13
[52] U.S. Cl. .......................................... 8/407; 8/406; 8/408; 8/409; 8/410; 8/411; 8/412
[58] Field of Search ................. 8/406, 407, 408, 409, 8/410, 411, 412

[56] References Cited

U.S. PATENT DOCUMENTS

| | | | |
|---|---|---|---|
| 3,674,414 | 7/1972 | Kalopissis et al. | 8/408 |
| 3,694,138 | 9/1972 | Kalopissis et al. | 8/408 |
| 3,893,803 | 7/1975 | Kaiser | 8/408 |

*Primary Examiner*—Donald B. Moyer
*Attorney, Agent, or Firm*—Hammond & Littell, Weissenberger and Muserlian

[57] ABSTRACT

This invention is directed to a composition of the developer-coupler type for the dyeing of hair, consisting essentially of, as coupler, at least on N-benzyl-m-phenylenediamine derivative of general formula

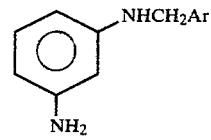

wherein Ar is a radical selected from the group consisting of

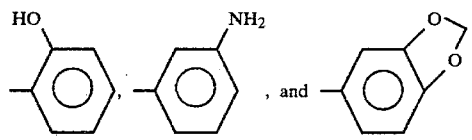

or an inorganic or organic acid salt thereof, and, as developer component, one or more of the conventional developer components used in oxidation dyes.

16 Claims, No Drawings

HAIR DYES

FIELD OF THE INVENTION

This invention is directed to hair dyes. More specifically, this invention is directed to agents for the oxidative dyeing of hair that are based on N-benzyl-m-phenylenediamine derivatives.

BACKGROUND OF THE INVENTION

Dyes known as oxidation dyes, which are produced by oxidative coupling of a developer component with a coupling component, are preferred due to their intense colors and very good fastness. Nitrogen bases such as p-phenylenediamine derivatives, diaminopyridines, 4-aminopyrazolone derivatives, and heterocyclic hydrazones are generally used as developer substances. Phenols, naphthols, resorcinol derivatives, and pyrazolones are useful as coupling components.

Good oxidation dyestuff components must meet the following requirements:

They must produce the desired color nuances in sufficient intensity during oxidative coupling with the respective developer or coupling component. Also, they must possess a capacity for being absorbed by human hair, which capacity ranges from sufficient to very good; and, in addition, they should be toxicologically and dermatologically safe. The production of the strongest possible color shades closely corresponding to the natural color nuances is also important. Further, the general stability of the dyestuff produced as well as their fastness to light and to washing and their thermostability, have very special significance for the prevention of color shifts from the original color nuance or even a change in color to different shades.

Thus, the search for suitable oxidation hair dyes includes the task of finding the proper components that meet the above-mentioned prerequisites in an optimal fashion.

OBJECTS OF THE INVENTION

It is an object of the invention to provide novel hair dyestuffs.

It is also an object of the invention to provide agents for the oxidative dyeing of hair that are based on N-benzyl-m-phenylenediamine derivatives.

It is a further object of the invention to provide a process for dyeing hair wherein a novel hair dyestuff is employed.

These and other objects of the invention will become more apparent in the discussion below.

DESCRIPTION OF THE INVENTION

Applicants have found novel hair dyestuffs that satisfy the above-mentioned requirements. The hair dyestuffs are based upon oxidation dyes comprising N-benzyl-m-phenylenediamine derivatives of the general formula

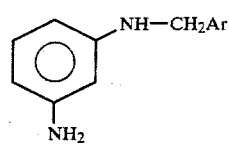

(I)

wherein Ar represents a radical selected from the group consisting of

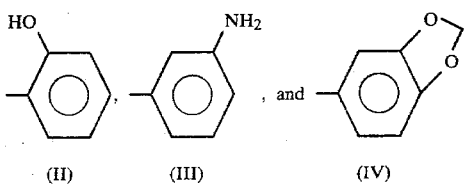

as well as the inorganic or organic acid salts thereof, as coupling components, and the developer components normally used in oxidation hair dyestuffs. Such hair dyestuffs can meet the above-mentioned requirements to an especially high degree.

Upon their use as coupling components together with developers generally used for oxidation hair dyes, the compounds of Formula I yield very intense color nuances ranging from green through brown to blue-black, and thus represent a considerable expansion of the possibilities in oxidative hair dyeing. In addition, the N-benzyl-m-phenylenediamine derivatives according to the invention are characterized by an exceptional fastness of the dyeing achieved with them, good solubility in water, good shelf life, and toxicological as well as dermatological safety.

The N-benzyl-m-phenylenediamine derivatives to be used as coupling components according to the invention may be used in that form or in the form of their salts with inorganic or organic acids. Such salts include, for example, chlorides, sulfates, phosphates, acetates, propionates, lactates, citrates, and the like.

The N-benzyl-m-phenylenediamine derivatives of Formula I to be used as coupling components according to the invention are basically known from Patent Specification No. 123 049 from the Democratic Republic of Germany. The derivatives can be prepared by the conventional methods known to those skilled in the art, such as, for example, by catalytic hydrogenation of the respective N-benzylidene anilines.

The products according to Patent Specification No. 123 049 may be used as plant growth regulators, herbicides, and algicides. Another possibility for the preparation of the N-benzyl-m-phenylenediamine derivatives according to conventional methods in the form of their hydrochlorides consists of the catalytic reduction of the respective Schiff's bases in ethanolic solution with palladium as catalyst and acidification of the hydrogenation product with hydrochloric acid prior to the evaporation of the solution. The Schiff's bases are prepared by the condensation of m-nitroaniline with the respective aromatic aldehyde in alcoholic solution or in toluene in the presence of 2% p-toluene sulfonic acid, with the release of water. The complete preparation is shown in the following diagram:

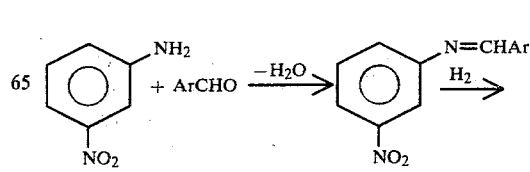

-continued

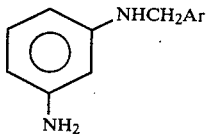

wherein Ar can be one of the radicals II, III, and IV described above. Thus, the derivatives to be used as coupling substances according to the invention are N-(2-hydroxybenzyl)-m-phenylenediamine, N-(3-aminobenzyl)-m-phenylenediamine, and N-piperonyl-m-phenylenediamine.

The developer components to be used according to the invention are those that are conventionally used in oxidative coupled dyestuffs. Examples of such developer components include primary aromatic amines with an additional functional group in the p-position, such as p-phenylenediamine, p-toluylenediamine, monochloro-p-phenylenediamine, p-dimethylaminoaniline, p-aminophenol, or p-diaminoanisol, or other compounds of this type which also contain one or more additional functional groups such as hydroxyl groups, amino groups, or NHR or NHR$_2$ groups, in which R represents an alkali metal or a hydroxyalkyl radical with from 1 to 4 carbon atoms. Diaminopyridine derivatives, heterocyclic hydrazone derivatives, and 4-amino-pyrazolone derivatives such as 4-amino-1-phenyl-3-carbamoyl-pyrazolone-5, are additional examples of useful developer components.

Further developer components that can be combined with the N-benzyl-m-phenylenediamine derivatives include tetraaminopyrimidines of the general formula

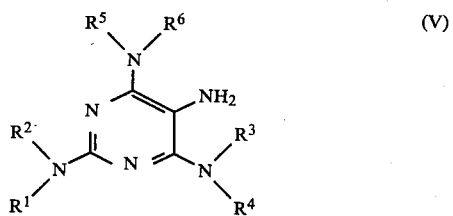

(V)

wherein R$^1$ to R$^6$ may each be a hydrogen atom; an alkyl radical having from 1 to 4 carbon atoms; or the radical —(CH$_2$)n—X in which n is an integer of from 1 to 4 and X is selected from the group consisting of a hydroxyl group, a halogen atom, and —NR$^7$R$^8$ in which R$^7$ and R$^8$ are each a hydrogen atom or an alkyl group having from 1 to 4 carbon atoms or together with the nitrogen atom R$^7$ and R$^8$ form a member selected from the group consisting of a 5 or 6 membered heterocyclic ring optionally containing an additional nitrogen atom or oxygen atom in the ring, as well as their inorganic or organic salts. See, for example, U.S. Pat. No. 4,003,699.

The tetraaminopyrimidines to be used as developer components may be used as such or in the form of their salts with inorganic or organic acids, such as, for example, chlorides, sulfates, phosphates, acetates, propionates, lactates, citrates, and the like.

Developer substances suitable for combination with the N-benzyl-m-phenylenediamine derivatives of Formula I to be used as coupling components according to the invention include, for example, the following:
2,4,5,6-tetraaminopyrimidine,
4,5-diamino-2,6-bismethylaminopyrimidine,
2,5-diamino-4,6-bismethylaminopyrimidine,
4,5-diamino-6-butylamino-2-dimethylaminopyrimidine,
2,5-diamino-4-diethylamino-6-methylaminopyrimidine,
4,5-diamino-6-diethylamino-2-dimethylaminopyrimidine,
4,5-diamino-2-diethylamino-6-methylaminopyrimidine,
4,5-diamino-2-dimethylamino-6-ethylaminopyrimidine,
4,5-diamino-2-dimethylamino-6-isopropylaminopyrimidine,
4,5-diamino-2-dimethylamino-6-methylaminopyrimidine,
4,5-diamino-6-dimethylamino-2-methylaminopyrimidine,
4,5-diamino-2-dimethylamino-6-propylaminopyrimidine,
2,4,5-triamino-6-dimethylaminopyrimidine,
4,5,6-triamino-2-dimethylaminopyrimidine,
2,4,5-triamino-6-methylaminopyrimidine,
4,5,6-triamino-2-methylaminopyrimidine,
4,5-diamino-2-dimethylamino-6-piperidinopyrimidine,
4,5-diamino-6-methylamino-2-piperidinopyrimidine,
2,4,5-triamino-6-piperidinopyrimidine,
2,4,5-triamino-6-anilinopyrimidine,
2,4,5-triamino-6-benzylaminopyrimidine,
2,4,5-triamino-6-benzylidenaminopyrimidine,
4,5,6-triamino-2-piperidinopyrimidine,
2,4,6-trismethylamino-5-aminopyrimidine,
2,4,5-triamino-6-di-n-propylaminopyrimidine,
2,4,5-triamino-6-morpholinopyrimidine,
2,5,6-triamino-4-dimethylaminopyrimidine,
4,5,6-triamino-2-morpholinopyrimidine,
2,4,5-triamino-6-β-hydroxyethylaminopyrimidine,
4,5,6-triamino-2-β-amino-ethylaminopyrimidine,
2,5,6-triamino-4-β-methylamino-ethylaminopyrimidine,
2,5-diamino-4,6-bis-gamma-diethylamino-propylaminopyrimidine,
4,5-diamino-2-methylamino-6-β-hydroxyethylaminopyrimidine,
5-amino-2,4,5-triethylaminopyrimidine, and
2,4-bis-β-hydroxyethylamino-6-anilino-5-aminopyrimidine.

The p-toluylenediamine has special significance as developer component since blue-black color nuances with great light fastness can be produced by its combination with the N-benzyl-m-phenylene-diamine derivatives of Formula I, which are very important in the practical application for the creation of natural brown tones, for example.

In the hair dyestuffs according to the invention, the coupling and developer components generally are used in approximately equimolar amounts. Although the equimolar use proves suitable, it is not disadvantageous to add the coupling component in a certain excess or deficiency. For example, the coupling and developer components can be present in a molar range of from about 2:1 to 1:2, a 10% or less excess or deficiency being preferred.

In addition, it is not necessary that the developer component and the coupling substance are homogeneous or pure products. On the contrary, the developer component may consist of mixtures of the developer compounds to be used according to the invention, and the coupling substance may represent mixtures of the N-benzyl-m-phenylenediamine derivatives to be used according to the invention. Furthermore, the hair dyestuffs according to the invention may also contain, if desired, conventional, directly applicable dyes in the mixture, provided that such is necessary for the creation of certain color nuances.

The oxidative coupling, that is, the development of the dye, can in principle be carried out with atmospheric oxygen, as is done with other oxidation hair dyestuff also. However, chemical oxidation agents are advantageously employed. Particularly suitable as such oxidation agents are hydrogen peroxide or its addition compounds with urea, melamine, or sodium borate as well as mixtures of such hydrogen peroxide adducts with potassium peroxydisulfate.

The dyes according to the invention are incorporated into respective cosmetic preparations such as creams, emulsions, gels, or also simple solutions for their use and are mixed with one of the mentioned oxidation agents immediately before application to the hair. The concentration of the coupling-developer combination in such dyes is from about 0.2 to 5 percent by weight, preferably from about 1 to 3 percent by weight, based on the total weight of the preparation.

For the preparation of creams, emulsions, or gels, the dye components are mixed with the other components normally used in such preparations. Such additional components include, for example, wetting or emulsifying agents of the anionic or nonionic type such as alkylbenzenesulfonates, sulfates of fatty alcohols, higher alkylsulfonates, alkanolamines of fatty acids, adducts of ethylene oxide with fatty alcohols, thickeners such as methyl cellulose, starch, higher fatty alcohols, paraffin oil, and fatty acids, and perfume oils and hair-conditioning and grooming agents such as pantothenic acid and cholesterol. The mentioned additives are added in the amounts normal for these purposes. For example, wetting and emulsifying agents can be present in concentrations of from about 0.5 to 30 percent by weight, preferably from about 1 to 15 percent by weight, and thickeners can be present in concentrations of from about 0.1 to 25 percent by weight, preferably from about 1 to 15 percent by weight, based, respectively, on the weight of the total preparation.

The dye according to the invention can be applied in a weakly acid, neutral or particularly alkaline medium at a pH of 8 to 10, regardless of whether it is a solution, an emulsion, a cream, or a gel. The application temperatures range from about 15° to 40° C., preferably at room temperature. After the dye is allowed to react for approximately 30 minutes, the preparation is removed by rinsing from the hair to be dyed. Then the hair is washed with a mild shampoo and dried.

The following examples are intended to illustrate the invention and are not be be construed as limiting the invention thereto.

EXAMPLES

The following compounds were used in the form of their hydrochlorides in the examples presented hereinafter:

Coupler component

K1 N-(2-hydroxybenzyl)-m-phenylenediamine dihydrochloride

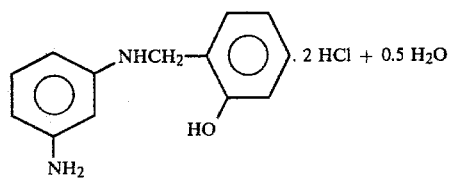

Melting point: 101° C., with decomposition.

K2 N-(3-aminobenzyl)-m-phenylenediamine trihydrochloride

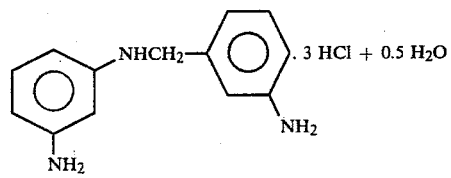

Melting point: 66°–70° C.

K3 N-piperonyl-m-phenylenediamine trihydrochloride

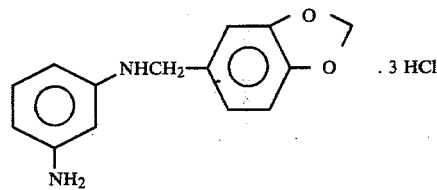

Melting point: from about 200° C., with decomposition.

Developer component

The following compounds were used as developer components in the examples hereinafter:
E1 2,4,5,6-tetraaminopyrimidine
E2 p-toluylenediamine

Procedure

The hair dyes according to the invention were used in the form of a cream emulsion. For this, 0.01 mol of the developer substances listed in the table below and N-benzyl-m-phenylenediamine derivatives, respectively, were worked into the emulsion containing
  10 parts by weight of fatty alcohols having 12 to 18 carbon atoms,
  10 parts by weight fatty alcohol sulfate (sodium salt) having 12 to 18 carbon atoms, and
  75 parts by weight water.

The pH of the emulsion was then adjusted to 9.5 with ammonia, and the emulsion was made up to 100 parts by weight with water. Oxidative coupling was carried out with a 1% hydrogen peroxide solution acting as oxidation agent, 10 parts by weight of the hydrogen peroxide solution being added to 100 parts by weight of the emulsion. The particular dyeing cream, with additional oxidation agent, was applied to human hair which was 90% grey and which had not been specially pretreated, and the cream was left on the hair for 30 minutes. After completion of the dyeing process, the hair was washed out with a regular shampoo and then dried. The colorations obtained by this process can be found in the table below.

TABLE

| Example | Developer | Coupler | Color Shade Obtained with 1% H$_2$O$_2$ Solution |
| --- | --- | --- | --- |
| 1 | E1 | K1 | dark-green |
| 2 | E2 | K1 | blue-black |
| 3 | E1 | K2 | olive brown |
| 4 | E2 | K2 | dark green |
| 5 | E1 | K3 | olive grey |
| 6 | E2 | K3 | blue-black |

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A composition of the developer-coupler type for the dyeing of human hair, consisting essentially of, as coupler, at least one N-benzyl-m-phenylenediamine derivative of the general formula

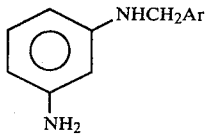

wherein Ar is a radical selected from the group consisting of

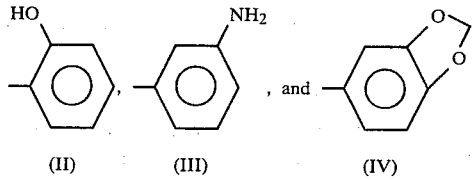

of a salt thereof, and, as developer component, one or more of the conventional developer components used in oxidation dyes, the molar ratio of the coupler to the developer being from about 2:1 to 1:2.

2. The composition of claim 1 wherein p-toluylenediamine is used as developer component.

3. The composition of claim 1 wherein the composition comprises from about 0.2 to 5 percent by weight of developer-coupler combination.

4. The composition of claim 3 wherein the composition comprises from about 1 to 3 percent by weight of developer-coupler combination.

5. The composition of claim 1, wherein the coupler is comprised of two or more N-benzyl-m-phenylenediamine derivatives or salts thereof.

6. The composition of claim 1 which additionally contains conventional additives selected from the group consisting of conventional couplers and conventional directly absorbing dyes.

7. A process for the dyeing of hair comprising applying to said hair, at temperatures ranging substantially from about 15° C. to 40° C. for a time sufficient to effect dyeing through oxidation, an effective amount of the developer-coupler composition according to claim 1 in an aqueous medium.

8. The process for the dyeing of hair of claim 7 wherein the oxidation is also effected by the action of a chemical oxidation agent.

9. The process of claim 8, wherein the chemical oxidation agent is selected from the group consisting of hydrogen peroxide or its addition compounds with urea, melamine, or sodium borate, and mixtures thereof with potassium peroxydisulfate.

10. The composition of claim 1, wherein the developer component comprises one or more compounds selected from the group consisting of
p-toluylenediamine,
2,4,5,6-tetraaminopyrimidine,
4,5-diamino-2,6-bismethylaminopyrimidine,
2,5-diamino-4,6-bismethylaminopyrimidine,
4,5-diamino-6-butylamino-2-dimethylaminopyrimidine,
2,5-diamino-4-diethylamino-6-methylaminopyrimidine,
4,5-diamino-6-diethylamino-2-dimethylaminopyrimidine,
4,5-diamino-2-diethylamino-6-methylaminopyrimidine,
4,5-diamino-2-dimethylamino-6-ethylaminopyrimidine,
4,5-diamino-2-dimethylamino-6-isopropylaminopyrimidine,
4,5-diamino-2-dimethylamino-6-methylaminopyrimidine,
4,5-diamino-6-dimethylamino-2-methylaminopyrimidine,
4,5-diamino-2-dimethylamino-6-propylaminopyrimidine,
2,4,5-triamino-6-dimethylaminopyrimidine,
4,5,6-triamino-2-dimethylaminopyrimidine,
2,4,5-triamino-6-methylaminopyrimidine,
4,5,6-triamino-2-methylaminopyrimidine,
4,5-diamino-2-dimethylamino-6-piperidinopyrimidine,
4,5-diamino-6-methylamino-2-piperidinopyrimidine,
2,4,5-triamino-6-piperidinopyrimidine,
2,4,5-triamino-6-anilinopyrimidine,
2,4,5-triamino-6-benzylaminopyrimidine,
2,4,5-triamino-6-benzylidenaminopyrimidine,
4,5,6-triamino-2-piperidinopyrimidine,
2,4,6-trismethylamino-5-aminopyrimidine,
2,4,5-triamino-6-di-n-propylaminopyrimidine,
2,4,5-triamino-6-morpholinopyrimidine,
2,5,6-triamino-4-dimethylaminopyrimidine,
4,5,6-triamino-2-morpholinopyrimidine,
2,4,5-triamino-6-β-hydroxyethylaminopyrimidine,
4,5,6-triamino-2-β-amino-ethylaminopyrimidine,
2,5,6-triamino-4-β-methylamino-ethylaminopyrimidine,
2,5-diamino-4,6-bis-gamma-diethylamino-propylaminopyrimidine,
4,5-diamino-2-methylamino-6-β-hydroxyethylaminopyrinidine,
5-amino-2,4,5-triethylaminopyrimidine, and
2,4-bis-β-hydroxyethylamino-6-anilino-5-aminopyrimidine.

11. The composition of claim 1, wherein Ar is the radical of Formula II.

12. The composition of claim 1, wherein Ar is the radical of Formula III.

13. The composition of claim 1, wherein Ar is the radical of Formula IV.

14. The composition of claim 1, which comprises
(1) from about 0.2 to 5 percent by weight of developer-coupler combination;
(2) from about 0.5 to 30 percent by weight of wetting and emulsifying agents;
(3) from about 0.1 to 25 percent by weight of thickeners; and (4) the balance water.

15. A process for the dyeing of hair comprising applying to said hair, at temperatures ranging substantially from about 15° to 40° C. at a pH of from about 8 to 10 for a time sufficient to effect dyeing through oxidation, an effective amount of the aqueous developer-coupler composition according to claim 10.

16. The process for the dyeing of hair of claim 15, wherein the oxidation is also effected by the action of a chemical oxidation agent selected from the group consisting of hydrogen peroxide and its addition agents with urea, melamine, or sodium borate, and mixtures thereof with potassium peroxydisulfate.

* * * * *

UNITED STATES PATENT AND TRADEMARK OFFICE
CERTIFICATE OF CORRECTION

PATENT NO. : 4,325,704
DATED : April 20, 1982
INVENTOR(S) : GÜNTHER KONRAD ET AL.

It is certified that error appears in the above—identified patent and that said Letters Patent is hereby corrected as shown below:

Title page [75]: The name of the first inventor should read

-- Günther Konrad --

Signed and Sealed this

Twenty-eighth Day of December 1982

[SEAL]

Attest:

GERALD J. MOSSINGHOFF

Attesting Officer    Commissioner of Patents and Trademarks